US008327851B2

(12) United States Patent
Connor

(10) Patent No.: US 8,327,851 B2
(45) Date of Patent: Dec. 11, 2012

(54) RESPIRATORY MASK WITH USER INTERFACE

(75) Inventor: Robert A. Connor, Minneapolis, MN (US)

(73) Assignee: Sleepnea LLC, Forest Lake, MN (US)

( * ) Notice: Subject to any disclaimer, the term of this patent is extended or adjusted under 35 U.S.C. 154(b) by 361 days.

(21) Appl. No.: 12/661,330

(22) Filed: Mar. 15, 2010

(65) Prior Publication Data

US 2011/0220112 A1 Sep. 15, 2011

(51) Int. Cl.
*A61M 16/06* (2006.01)
(52) U.S. Cl. .......... 128/206.24; 128/201.23; 128/206.21
(58) Field of Classification Search ............. 128/201.23, 128/203.29, 205.25, 206.14, 206.21, 206.23, 128/206.24, 206.28, 207.11
See application file for complete search history.

(56) References Cited

U.S. PATENT DOCUMENTS

| | | |
|---|---|---|
| 3,330,274 A | 7/1967 | Bennett |
| 3,982,532 A | 9/1976 | Halldin et al. |
| 4,069,516 A | 1/1978 | Watkins, Jr. |
| 4,657,010 A | 4/1987 | Wright |
| 4,907,584 A | 3/1990 | McGinnis |
| 4,915,106 A | 4/1990 | Aulgur et al. |
| 4,971,051 A | 11/1990 | Toffolon |
| 5,074,297 A | 12/1991 | Venegas |
| 5,243,971 A | 9/1993 | Sullivan et al. |
| 5,465,712 A | 11/1995 | Malis et al. |
| 5,492,116 A | 2/1996 | Scarberry et al. |
| 5,503,147 A | 4/1996 | Bertheau |
| 5,540,223 A | 7/1996 | Starr et al. |
| 5,560,354 A | 10/1996 | Berthon-Jones et al. |
| 5,570,689 A | 11/1996 | Starr et al. |
| 5,647,357 A | 7/1997 | Barnett et al. |
| 5,655,527 A | 8/1997 | Scarberry et al. |
| 5,662,101 A | 9/1997 | Ogden et al. |
| 5,673,690 A | 10/1997 | Tayebi et al. |
| 5,699,791 A | 12/1997 | Sukiennik et al. |
| 5,746,201 A | 5/1998 | Kidd |
| 5,832,918 A | 11/1998 | Pantino |
| 5,884,624 A | 3/1999 | Barnett et al. |
| 5,887,587 A | 3/1999 | Groenke |
| 5,921,239 A | 7/1999 | McCall et al. |
| 6,019,101 A | 2/2000 | Cotner et al. |
| 6,112,746 A | 9/2000 | Kwok et al. |
| 6,192,886 B1 | 2/2001 | Rudolph |
| 6,196,223 B1 | 3/2001 | Belfer et al. |
| 6,341,606 B1 | 1/2002 | Bordewick et al. |
| 6,357,441 B1 | 3/2002 | Kwok et al. |
| 6,397,847 B1 | 6/2002 | Scarberry et al. |
| 6,412,488 B1 | 7/2002 | Barnett et al. |

(Continued)

*Primary Examiner* — Nicholas Lucchesi
*Assistant Examiner* — Gerald Landry, II

(57) ABSTRACT

This invention is a respiration-related mask with a user interface for custom fitting the mask to a person's face. It comprises: a respiration-related mask that directs a breathable gas into a person's nose, mouth, or both; two or more differentially and selectively movable members that are part of the mask, wherein differential and selective movement of these members changes the face-contacting contour of the mask; and a remote user interface that allows the person to differentially and selectively adjust the movable members so as to better fit the face-contacting contour of the mask to the person's face while the person is wearing the mask. The resulting mask can conform to the contours of a person's face so that there are no places around the mask that fit too tightly (causing irritation, skin marks, and pain) and no places that fit too loosely (causing air leaks). This can increase patient tolerance of wearing a mask and can improve the therapeutic efficiency of wearing a mask.

19 Claims, 4 Drawing Sheets

U.S. PATENT DOCUMENTS

| | | | |
|---|---|---|---|
| 6,418,928 B1 | 7/2002 | Bordewick et al. |
| 6,425,395 B1 | 7/2002 | Brewer et al. |
| 6,464,924 B1 | 10/2002 | Thornton |
| 6,467,483 B1 | 10/2002 | Kopacko et al. |
| 6,513,526 B2 | 2/2003 | Kwok et al. |
| 6,530,373 B1 | 3/2003 | Patron et al. |
| 6,581,602 B2 | 6/2003 | Kwok et al. |
| 6,615,834 B2 | 9/2003 | Gradon et al. |
| 6,631,718 B1 | 10/2003 | Lovell |
| 6,634,358 B2 | 10/2003 | Kwok et al. |
| 6,651,663 B2 | 11/2003 | Barnett et al. |
| 6,701,926 B2 | 3/2004 | Olsen et al. |
| 6,728,589 B1 | 4/2004 | Delache et al. |
| 6,729,333 B2 | 5/2004 | Barnett et al. |
| 6,772,760 B2 | 8/2004 | Frater et al. |
| 6,789,541 B2 | 9/2004 | Olsen et al. |
| 6,843,249 B2 | 1/2005 | Bergamaschi et al. |
| 6,851,428 B2 | 2/2005 | Dennis |
| 6,854,465 B2 | 2/2005 | Bordewick et al. |
| 6,857,428 B2 | 2/2005 | Thornton |
| 6,886,564 B2 | 5/2005 | Sullivan et al. |
| 6,895,965 B2 | 5/2005 | Scarberry et al. |
| 6,951,218 B2 | 10/2005 | Gradon et al. |
| 6,959,710 B2 | 11/2005 | Barnett et al. |
| 6,981,502 B2 | 1/2006 | McCormick et al. |
| 6,986,352 B2 | 1/2006 | Frater et al. |
| 7,007,696 B2 | 3/2006 | Palkon et al. |
| 7,021,311 B2 | 4/2006 | Gunaratnam et al. |
| 7,021,312 B2 | 4/2006 | Cannon |
| 7,044,130 B2 | 5/2006 | Jones, Jr. et al. |
| 7,069,933 B2 | 7/2006 | Kwok et al. |
| 7,107,989 B2 | 9/2006 | Frater et al. |
| 7,121,279 B2 | 10/2006 | Dennis |
| 7,171,966 B2 | 2/2007 | Schrader et al. |
| 7,178,527 B2 | 2/2007 | Kwok et al. |
| 7,219,670 B2 | 5/2007 | Jones, Jr. et al. |
| 7,237,551 B2 | 7/2007 | Ho et al. |
| 7,243,650 B2 | 7/2007 | Thornton |
| 7,243,651 B2 | 7/2007 | Kwok et al. |
| 7,273,052 B2 | 9/2007 | Gossweiler |
| 7,287,528 B2 | 10/2007 | Ho et al. |
| 7,308,895 B2 | 12/2007 | Wixey et al. |
| 7,318,439 B2 | 1/2008 | Raje et al. |
| 7,320,323 B2 | 1/2008 | Lang et al. |
| 7,353,827 B2 | 4/2008 | Geist |
| 7,455,063 B2 | 11/2008 | Geiselhart et al. |
| 7,472,703 B2 | 1/2009 | Hernandez et al. |
| 7,481,221 B2 | 1/2009 | Kullik et al. |
| 7,503,327 B2 | 3/2009 | Gunaratnam |
| 7,523,754 B2 | 4/2009 | Lithgow et al. |
| 7,546,837 B2 | 6/2009 | Busch et al. |
| 2005/0199240 A1 | 9/2005 | Hall |
| 2006/0027236 A1 | 2/2006 | Barnett et al. |
| 2006/0027237 A1 | 2/2006 | Sleeper et al. |
| 2006/0032504 A1 | 2/2006 | Burton et al. |
| 2006/0118117 A1 | 6/2006 | Berthon-Jones et al. |
| 2006/0235877 A1 * | 10/2006 | Richard et al. .............. 707/104.1 |
| 2006/0283456 A1 | 12/2006 | Geiselhart et al. |
| 2008/0035152 A1 | 2/2008 | Ho et al. |
| 2008/0053446 A1 | 3/2008 | Sleeper et al. |
| 2008/0060652 A1 * | 3/2008 | Selvarajan et al. ...... 128/206.21 |
| 2008/0060653 A1 | 3/2008 | Hallett et al. |
| 2008/0230068 A1 | 9/2008 | Rudolph |
| 2009/0020127 A1 * | 1/2009 | Boone et al. ............. 128/207.14 |
| 2009/0078267 A1 | 3/2009 | Burz et al. |
| 2009/0095301 A1 | 4/2009 | Hitchcock et al. |
| 2009/0107506 A1 | 4/2009 | Collazo et al. |
| 2009/0159084 A1 | 6/2009 | Sher et al. |
| 2010/0229867 A1 * | 9/2010 | Bertinetti et al. ........ 128/205.25 |
| 2012/0111331 A1 * | 5/2012 | Witt et al. ................ 128/205.25 |

\* cited by examiner

RESPIRATORY MASK WITH USER INTERFACE

CROSS-REFERENCE TO RELATED APPLICATIONS

This patent application claims the priority benefit of U.S. patent application Ser. No. 12/589,405 entitled "Respiratory Mask with Adjustable Shape" filed on Oct. 23, 2009 by Robert A. Connor.

FEDERALLY SPONSORED RESEARCH

Not Applicable

SEQUENCE LISTING OR PROGRAM

Not Applicable

BACKGROUND

1. Field of Invention

This invention relates to masks that assist respiration.

2. Background

Obstructive Sleep Apnea (OSA) is intermittent blockage of a person's airflow while they sleep due to movement of their tongue or other soft tissue. Such blockages can happen hundreds of times each night, causing poor sleep and oxygen deprivation. Basically, the person temporarily stops breathing during each blockage. Unfortunately, the person might not even be aware of this serious problem because they never fully wake up during blockages.

Obstructive sleep apnea can cause serious long-term harmful effects. These harmful effects include: disrupted sleep; chronic fatigue; morning headaches; irritability; brain damage; cognitive dysfunction; impotency; high blood pressure; heart attacks; congestive heart failure; motor vehicle crashes; job-site accidents; and even death. Despite these harmful effects, it is estimated that only 5% to 8% of the affected population are treated. Approximately 20 million Americans and 35 million people worldwide have obstructive sleep apnea and the number is growing rapidly.

The first-line therapy for most people who are diagnosed with obstructive sleep apnea is Continuous Positive Airway Pressure (CPAP). CPAP keeps the airway open with a stream of pressurized air that is channeled into a person's nose (or nose and mouth) while they sleep. The positive pressure keeps their tongue and other soft tissue from blocking the airway. A CPAP machine continuously pumps pressurized air into a CPAP mask that fits over a person's face while they sleep. Some CPAP masks cover only the sleeper's nose. Other CPAP masks cover both the sleeper's nose and mouth.

In many respects, the mask is the weak link of CPAP. CPAP only works if a person tolerates wearing the CPAP mask and if the mask does not leak pressurized air. If the mask fits too tightly in some places where the mask presses against the person's face, then this can cause skin irritation, red marks, and pain. These problems contribute to high non-compliance with CPAP therapy; many people are not willing to wear a CPAP mask while they sleep. Estimates of the percentage of people who should wear CPAP masks but do not wear them range as high as 50%. On the other hand, if the mask fits too loosely and there are gaps in some places between the mask and the person's face, then the mask leaks pressurized air. Air leaks erode the clinical effectiveness, of CPAP.

The main challenge for designing a CPAP mask is how to create a mask that closely conforms to the contours of an individual's face while they sleep so that there are no places around the mask that fit too tightly (causing irritation, skin marks, and pain) and no places that fit too loosely (causing air leaks). This challenge is especially difficult because different people can have quite different facial contours. Also, facial tissue contours can change during sleep. For example, facial contours can shift as a person rests their head and face on a pillow, particularly for people who sleep on their side or on their stomach. The ideal CPAP mask should not only be adjustable to custom fit the contours of an individual's face, but should also adjust to changes in that person's facial contours while the person sleeps.

There are various approaches in the prior art that attempt to address this main challenge for CPAP design. These approaches include: masks with adjustable straps; masks whose overall size can be manually adjusted; masks with a cushion seal filled with a gas, liquid, or gel; masks with an inflatable single-compartment cushion seal; masks that are custom fitted for a person's face by pressing moldable material against their face; and masks that are custom fitted for a person's face using three-dimensional facial imaging and custom fabrication. Some prior art combines two or more of these approaches. For example, one can design a mask with both adjustable straps and a gel cushion.

However, none of the approaches in the prior art have solved the main challenge of how to create a CPAP mask that conforms and adapts to the contours of an individual's face while they are wearing the mask. Accordingly, skin irritation from tight places around CPAP mask perimeters and air leaks from loose places around CPAP mask perimeters remain ongoing problems in CPAP therapy. There is still a clinical need for an innovative CPAP mask to correct these problems. This need is met by the invention disclosed herein. This invention can custom fit a CPAP mask to the contours of particular individual's face while the person is wearing the mask, even while they sleep. This invention can achieve uniform pressure on the person's face around the entire perimeter of the mask to reduce skin irritation and air leaks. This can increase patient compliance with CPAP therapy and reduce obstructive sleep apnea's harmful effects.

We now review the five general approaches that have been pursued in the prior art to address these CPAP mask problems and discuss the limitations of each approach. Then we introduce the invention disclosed herein and discuss how it addresses the limitations of these approaches in the prior art.

REVIEW OF RELATED ART

1. Manually-Adjustable Mask Straps

One of the most common approaches to fitting a CPAP mask to a person's face is to use adjustable straps or other adjustable means by which the main body of the mask is attached to a person's head. By manually tightening or loosening these straps, a person can adjust the overall pressure and the overall angle of the main body of the mask that presses against their face. Such gross adjustments of overall mask pressure and angle can correct large-scale air leakage and mask tightness, but do not provide localized control of the shape of the mark perimeter to selectively correct smaller-scale air leaks and tight spots. Even if a mask has a compressible or stretchable seal, adjustable straps provide only limited ability to change the actual shape of the mask perimeter in order to fit the specific contours of an individual's face.

For example, a person may have both concave and convex facial features in the same area near an adjustable strap; the person may have a fold in their skin next to the bridge of their nose or a wrinkle in their skin next to a high cheek bone. If this person adjusts the strap to make it loose, then air leaks out through the concave feature of their face. If the person adjusts the strap to make it tight, then the mask pinches the skin on the convex feature of their face. Ideally, the person would like a mask that allows them to expand only the segment of the mask perimeter above the concave feature and to shrink only the segment of the mask above the convex feature. However, adjustable straps do not provide such localized control of the shape of the mask perimeter.

As another limitation, manually-adjustable straps do not enable real-time adjustment of a CPAP mask in response to changes in a person's facial contours while they are sleeping. For example, when a person tosses and turns in their sleep, the soft tissue of their face can be compressed intermittently. This is especially true when a person sleeps on their side or stomach and presses their face against a pillow. This facial compression changes the contours of their face which can create tight spots or air leaks that did not exist when the person manually adjusted the mask straps before going to bed. Manually-adjustable straps do not correct tight spots or air leaks that happen during the night. Ideally, one would like a CPAP mask that could automatically adjust perimeter shape to correct tightness or air leaks in real time.

There are a large number of examples of CPAP masks in the prior art that use manually-adjustable straps to fit the main body of the mask to a person's face. Some of the most innovative examples include: U.S. Pat. No. 4,915,106 (Aulgur et al., 1990), U.S. Pat. No. 5,503,147 (Bertheau, 1996), and U.S. Pat. No. 6,886,564 (Sullivan et al., 2005), and U.S. Patent Application 20060032504 (Burton et al., 2006).

2. Compressible Seal or Single-Compartment Inflatable Seal

Another approach to fitting a CPAP mask to an individual's face is to use a compressible seal or a single-compartment inflatable seal between the mask perimeter and the person's face. Compressible seals are intended to passively conform to the contours of a person's face when they are pressed against a person's face. Single-compartment inflatable seals supplement passive compression from contact with a person's face with active expansion by inflation of a cushion seal. Compressible seals may be flexible hollow structures, structures filled with compressible foam, or cushions filled with air, liquid, or gel. Single-compartment inflatable seals may be cushions inflated with air, liquid, or gel. Either type of seal may be used in combination with adjustable straps.

Compressible or single-compartment inflatable seals provide some degree of mask perimeter flexibility to conform to the contours of an individual's face. Single-compartment inflatable seals offer greater control for adjusting overall pressure between the mask and face than do seals based on compression alone. However, like adjustable straps, compressible or single-compartment inflatable seals do not provide localized control of the shape of the mark perimeter to selectively correct smaller-scale air leaks and tight spots.

For example, suppose that there is an air leak at one location of the mask perimeter because of a gap between the mask and the person's face due to a crease in the person's facial tissue. The rest of the mask fits snugly and comfortably. With a single-component inflatable seal, one may be able to inflate the cushion seal sufficiently to eliminate the gap and air leak, but this can make the rest of the mask uncomfortable tight. With uniform inflation of a single component seal, there is no way to target expansion or contraction of certain places along the mask perimeter in order to precisely match an individual's facial contours.

Examples of CPAP masks in the prior art that appear to use a compressible seal or a single-compartment inflatable seal include the following U.S. Pat. No. 3,330,274 (Bennett, 1967), U.S. Pat. No. 3,982,532 (Halldin et al., 1976), U.S. Pat. No. 4,069,516 (Watkins Jr., 1978), U.S. Pat. No. 4,907,584 (McGinnis, 1990), U.S. Pat. No. 4,971,051 (Toffolon, 1990), U.S. Pat. No. 5,074,297 (Venegas, 1991), U.S. Pat. No. 5,243,971 (Sullivan et al., 1993), U.S. Pat. No. 5,465,712 (Malis et al., 1995), U.S. Pat. No. 5,492,116 (Scarberry et al., 1996), U.S. Pat. No. 5,540,223 (Starr et al., 1996), U.S. Pat. No. 5,560,354 (Berthon-Jones et al., 1996), U.S. Pat. No. 5,647,357 (Barnett et al., 1997), U.S. Pat. No. 5,655,527 (Scarberry et al., 1997), U.S. Pat. No. 5,662,101 (Ogden et al., 1997), U.S. Pat. No. 5,699,791 (Sukiennik et al., 1997), U.S. Pat. No. 5,746,201 (Kidd, 1998), U.S. Pat. No. 5,884,624 (Barnett et al., 1999), U.S. Pat. No. 5,887,587 (Groenke, 1999), U.S. Pat. No. 6,019,101 (Cotner et al., 2000), U.S. Pat. No. 6,112,746 (Kwok et al., 2000), U.S. Pat. No. 6,196,223 (Belfer et al., 2001), U.S. Pat. No. 6,341,606 (Bordewick et al., 2002), U.S. Pat. No. 6,357,441 (Kwok et al., 2002), U.S. Pat. No. 6,397,847 (Scarberry et al., 2002), U.S. Pat. No. 6,412,488 (Barnett et al., 2002), U.S. Pat. No. 6,418,928 (Bordewick et al., 2002), U.S. Pat. No. 6,425,395 (Brewer et al., 2002), U.S. Pat. No. 6,467,483 (Kopacko et al., 2002), U.S. Pat. No. 6,513,526 (Kwok et al., 2003), and U.S. Pat. No. 6,530,373 (Patron et al., 2003).

The list of examples of CPAP masks in the prior art that appear to use a compressible seal or a single-compartment inflatable seal continues with the following U.S. Pat. No. 6,581,602 (Kwok et al., 2003), U.S. Pat. No. 6,615,834 (Gradon et al., 2003), U.S. Pat. No. 6,631,718 (Lovell, 2003), U.S. Pat. No. 6,634,358 (Kwok et al., 2003), U.S. Pat. No. 6,651,663 (Barnett et al., 2003), U.S. Pat. No. 6,701,926 (Olsen et al., 2004), U.S. Pat. No. 6,729,333 (Barnett et al., 2004), U.S. Pat. No. 6,772,760 (Frater et al., 2004), U.S. Pat. No. 6,789,541 (Olsen et al., 2004), U.S. Pat. No. 6,854,465 (Bordewick et al., 2005), U.S. Pat. No. 6,895,965 (Scarberry et al., 2005), U.S. Pat. No. 6,951,218 (Gradon et al., 2005), U.S. Pat. No. 6,959,710 (Barnett et al., 2005), U.S. Pat. No. 6,981,502 (McCormick et al., 2006), U.S. Pat. No. 6,986,352 (Frater et al., 2006), U.S. Pat. No. 7,007,696 (Palkon et al., 2006), U.S. Pat. No. 7,021,311 (Gunaratnam et al., 2006), U.S. Pat. No. 7,021,312 (Cannon, 2006), U.S. Pat. No. 7,044,130 (Jones Jr. et al., 2006), U.S. Pat. No. 7,069,933 (Kwok et al., 2006), U.S. Pat. No. 7,107,989 (Frater et al., 2006), U.S. Pat. No. 7,171,966 (Schrader et al., 2007), U.S. Pat. No. 7,178,527 (Kwok et al., 2007), U.S. Pat. No. 7,219,670 (Jones, Jr. et al., 2007), U.S. Pat. No. 7,237,551 (Ho et al., 2007), U.S. Pat. No. 7,243,651 (Kwok et al., 2007), U.S. Pat. No. 7,273,052 (Gossweiler, 2007), U.S. Pat. No. 7,287,528 (Ho et al., 2007), U.S. Pat. No. 7,308,895 (Wixey et al., 2007), U.S. Pat. No. 7,318,439 (Raje et al., 2008), U.S. Pat. No. 7,320,323 (Lang et al., 2008), U.S. Pat. No. 7,353,827 (Geist, 2008), U.S. Pat. No. 7,455,063 (Geiselhart et al., 2008), U.S. Pat. No. 7,472,703 (Hernandez et al., 2009), U.S. Pat. No. 7,481,221 (Kullik et al., 2009), U.S. Pat. No. 7,503,327 (Gunaratnam, 2009), U.S. Pat. No. 7,523,754 (Lithgow et al., 2009), and U.S. Pat. No. 7,546,837 (Busch et al., 2009).

The list of examples of CPAP masks in the prior art that appear to use a compressible seal or a single-compartment inflatable seal continues with the following U.S. Patent Applications: 20050199240 (Hall, Matthew, 2005), 20060027236 (Barnett et al., 2006), 20060027237 (Sleeper et al., 2006), 20060283456 (Geiselhart et al., 2006), 20080035152 (Ho et al., 2008), 20080053446 (Sleeper et al., 2008), 20080060653 (Hallett et al., 2008), 20080230068 (Rudolph, 2008), 20090078267 (Burz et al., 2009), 20090095301 (Hitchcock et al., 2009), 20090107506 (Collazo et al., 2009), and 20090159084 (Sher et al., 2009).

3. Manually-Adjustable Overall Mask Size

Another approach to fitting a CPAP mask to an individual's face involves manual adjustment of the overall mask size. Manual adjustment of overall mask size can be done using Velcro straps, sliding snaps, accordion-like folds, vertically-adjustable spacers, or similar methods. Changing overall mask size is very useful for making a "one-size-fits-all" mask that can be adjusted for either adult or pediatric use.

However, the ability to change overall mask size provides only limited ability to change the shape of the mark perimeter to custom fit the contours of an individual's face. There is a lot more variation in facial contours between people other than vertical or horizontal dimensions. Also, the manual aspect of these adjustments does not enable adjustment of the mask in response to facial contour changes while a person sleeps. Accordingly, while masks with manual adjustments of overall mask size are useful for reducing the need to stock different size masks, they do not eliminate tight spots and leaks due to different facial contours.

Examples of CPAP masks in the prior art that appear to offer manual adjustment of overall mask size include the following: U.S. Pat. No. 4,657,010 (Wright, 1987), U.S. Pat. No. 5,570,689 (Starr et al., 1996), U.S. Pat. No. 5,673,690 (Tayebi et al., 1997), U.S. Pat. No. 5,921,239 (McCall et al., 1999), U.S. Pat. No. 6,192,886 (Rudolph, 2001), U.S. Pat. No. 6,851,428 (Dennis, 2005), and U.S. Pat. No. 7,121,279 (Dennis, 2006), and U.S. Patent Application 20060118117 (Berthon-Jones et al., 2006).

4. Customized One-Time Molding Process

Another approach to fitting a CPAP mask to a person's face is by using a one-time molding process with a soft material that hardens. For example, this process can involve: pressing a moldable material, when it is soft, against a person's face so that it matches the contours of the person's face; removing the material from the person's face; allowing the material to harden; and using the material, directly or indirectly, to create a customized mask that exactly fits the contours of that person's face. Unlike the above approaches, this approach can change the shape of the mask perimeter to fit the individual contours of a person's face. However, even this approach has limitations.

One limitation of approach is that a one-time molding process does not provide adjustments for how the mask fits when it is actually being worn. For example, when the mask is actually being worn, it may press against the person's face with a different pressure level, or at a different angle, than the manner in which the moldable material is pressed against the person's face. As another example, a person's facial contours may change due to short-term changes in retention of body fluids or longer-term changes in body weight. As another example, a person's facial contours may change during the night as their face comes into contact with a pillow. Ideally, one would want a CPAP mask whose shape can be continually adjusted to a person's changing facial contours while the person wears the mask, even while they sleep.

Other limitations of the one-time molding approach relate to the expense and inconvenience of the custom molding process. For example, it is unlikely that a person could self-administer the custom molding process. Thus they likely require assistance by another person, such as a health care professional, which can make the whole process expensive and time-consuming. Further, the molding process may involve: exposing the person's skin or lungs to chemicals in the moldable material; the delay of waiting for the moldable substance to harden; and unintended changes in the shape of the mask between when it is removed from the person's face and when it hardens. Ideally, one would want a CPAP mask that easily and continuously adjusts to a person's facial contours, without the involvement and expense of another person.

Examples of CPAP masks in the prior art that appear to use one-time moldable material include the following: U.S. Pat. No. 5,832,918 (Pantino, 1998), U.S. Pat. No. 6,397,847 (Scarberry et al., 2002), U.S. Pat. No. 6,464,924 (Thornton, 2002), U.S. Pat. No. 6,843,249 (Bergamaschi et al., 2005), U.S. Pat. No. 6,857,428 (Thornton, 2005), U.S. Pat. No. 6,895,965 (Scarberry et al., 2005), and U.S. Pat. No. 7,243,650 (Thornton, 2007).

5. Customized Fabrication using 3D Imaging

Another approach to fitting a CPAP mask to a person's face is by using three-dimensional medical imaging and custom fabrication of a mask based on the results of that imaging. In some respects, this is a virtual variation on the one-time molding process, one in which the molding process is done digitally rather than physically. Accordingly, fabrication by 3D imaging has advantages and limitations that are similar to those of a one-time molding process.

Limitations of this approach include: differences in facial contours when a mask is pressed against one's face vs. facial contours during imaging without anything pressed against one's face; changes in facial contours during sleep; and the time and expense involved in 3D medical imaging and custom fabrication. Custom fabrication using 3D imaging is less common than the four approaches described above, but an example of prior art that appears to use custom fabrication using 3D imaging is U.S. Pat. No. 6,728,589 (Delache et al., 2004).

SUMMARY AND ADVANTAGES OF THIS INVENTION

This invention is a respiration-related mask with a user interface for custom fitting the mask to a person's face. It comprises: a respiration-related mask that directs a breathable gas into a person's nose, mouth, or both; two or more differentially and selectively movable members that are part of the mask, wherein differential and selective movement of these members changes the face-contacting contour (perimeter) of the mask; and a remote user interface that allows the person to differentially and selectively adjust the movable members so as to better fit the face-contacting contour of the mask to the person's face while the person is wearing the mask. The resulting mask can conform to the contours of a person's face so that there are no places around the mask that fit too tightly (causing irritation, skin marks, and pain) and no places that fit too loosely (causing air leaks). This can increase patient tolerance of wearing a mask and can improve the therapeutic efficiency of wearing a mask.

This invention has several advantages over masks in the prior art. Having differentially and selectively movable members around the face-contacting contour (perimeter) of the mask allows a better and more comfortable seal than is possible with methods that rely on straps to hold the mask against one's face. One can adjust the overall position and pressure of a standard respiratory mask by adjusting straps, but there are limits to how accurately the straps can change the face-contacting contour of a standard mask. With straps, one may not be able to correct various spots around the mask perimeter with too little pressure (causing leaks) or too much pressure. (causing pain and skin irritation) based on the unique contours of one's face. Having differentially and selectively adjustable members around the perimeter of the mask also allows a better seal than is possible with a single inflatable ring or a single compressible gel ring. With a single inflatable ring, it can be difficult or impossible to find a single inflation pressure that stops leaks at spots where there is a gap between the mask surface and face without pinching or overly compressing the skin at other spots. Having differentially and selectively adjustable members around the perimeter of the mask also is also superior to methods using a one-time face-molding process to create a custom-fitted mask because this present invention: allows real-time adjustment of the contours of the mask while it is being worn; and avoids the time and expense of the custom molding process.

INTRODUCTION TO THE FIGURES

These figures show examples of how this invention may be embodied, but do not limit the full generalizability of the claims.

DETAILED DESCRIPTION OF THE FIGURES

These figures show different examples of how this invention may be embodied. However, these examples are not exhaustive. These figures do not limit the full generalizability of the claims.

Figure 1:
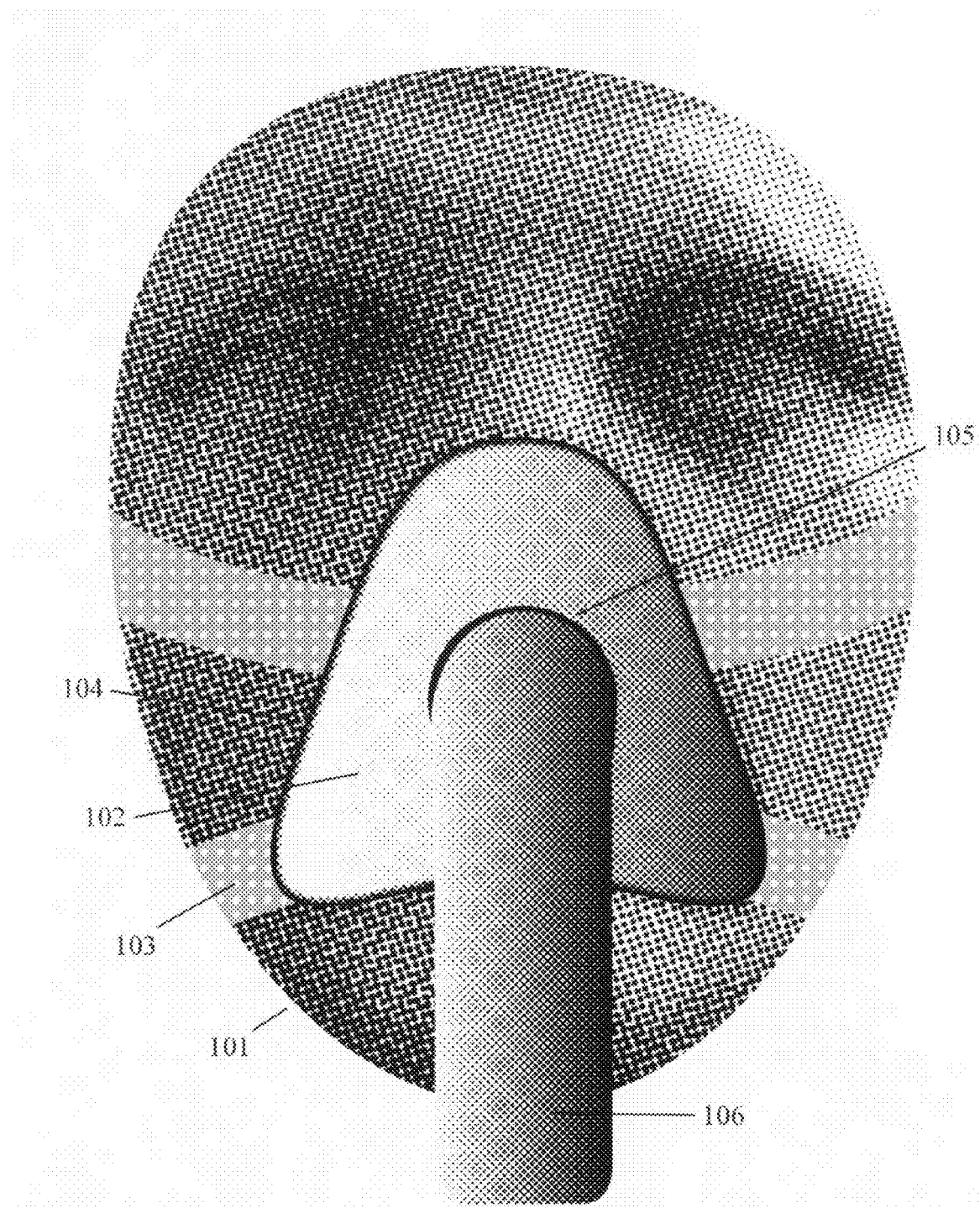
FIG. 1 shows a relatively-generic respiratory-assisting mask to provide context for this invention.

FIG. 1 shows a picture of a relatively-generic respiratory-assisting mask in order to provide context for introducing the novel aspects of this invention. However, FIG. 1 in itself, with its opaque frontal perspective, does not show the novel aspects of this invention. FIG. 1 shows an opaque frontal perspective of one example of a relatively-generic respiratory-assisting mask wherein the mask: covers a person's nose and mouth; is attached to the person's head with upper and lower straps; and has a single, centrally-connected tube through which a breathable gas can flow to the person's nose and mouth. In particular, FIG. 1 shows: the face 101 of the person wearing the mask; the main body 102 of the mask that forms a compartment containing breathable gas that covers the person's nose and mouth; the face-contacting contour (perimeter) 104 of the mask that forms a seal between mask 102 and the person's face 101; straps, including 103, that attach the main body of the mask 102 to the person's head; breathable gas tube 106; and central connection 105 that connects the mask 102 to the breathable gas tube 106. Central mask body 102 and breathable gas tube 106 may be made from materials selected from the group consisting of: ethylene propylene diene monomer, latex, silicone, polyvinyl chloride, and polyurethane.

A relatively-generic respiratory-assisting mask such the one shown in FIG. 1 may have several different applications and these different applications may require different components to be connected to the other end of breathable gas tube 106. In an example, if the mask is used in the treatment of sleep apnea, then the other end of breathable gas tube 106 would be connected to a pump that delivers pressurized air through the tube. In another example, for therapeutic delivery of oxygen-enriched air, the other end of breathable gas tube 106 would be connected to a device that blends ambient air with oxygen from a tank. In another example, for filtering air in settings with poor-quality ambient air, the other end of breathable gas tube 106 may be connected to an air pump and filter that removes impurities from the air. There are many different means in the prior art for pumping air, for storing and blending oxygen with ambient air, and for filtering out impurities from ambient air. Further, the specifics of how these functions may be performed are not central to this invention. Accordingly, a particular component at the other end of tube 106 is not specified in these figures.

In this example, the respiratory-assisting mask covers both the person's nose and mouth. In other examples, the respiratory-assisting mask may cover only the person's nose or only the person's mouth. In this example, the main body of the mask 102 is attached to the person's head with upper and lower straps, including strap 103. The exact method by which the mask is attached to the person's head is not central to this invention. In other examples, the mask may be attached to the person's head by means selected from the group consisting of: other types of straps, cantilevered rods, springs, belts and buckles, hook and loop fasteners, buttons, headbands, hats, and helmets. In this example, there is one centrally-connected tube 106 that comes up from below the face to deliver a breathable gas to the person. The exact method by which breathable gas is delivered to the main body of the mask 102 is not central to this invention. In other examples, there may be: one central tube that comes down from the top of the person's head to deliver breathable gas; or more than one tube delivering breathable gas from different angles.

Figure 2:
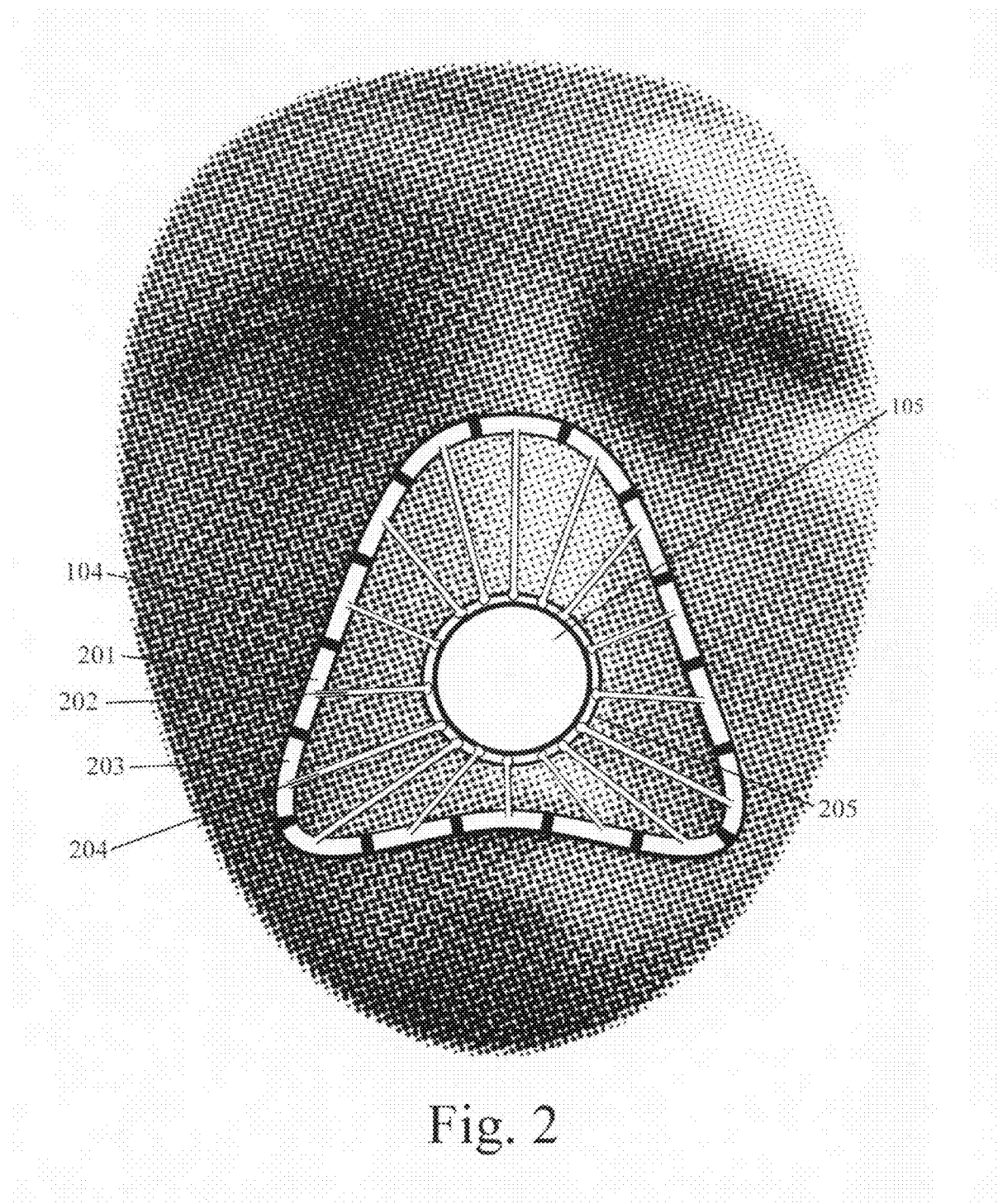
FIG. 2 shows this respiratory mask as if it were transparent except for: inflatable compartments around the contour of the mask; small tubes that connect with the inflatable compartments; a central connector between the mask and a breathable gas tube; and an outer ring around the central connector.

FIG. 2 shows a partially-transparent view of the respiratory mask that was shown in FIG. 1. This view of the mask shows some of the novel features of this invention. In particular, FIG. 2 shows the mask as if it were transparent except for: a series of contiguous inflatable compartments (including 201 and 203) around the face-contacting contour (perimeter) of the mask; a series of small tubes (including 202 and 204) that radiate from the center of the mask to connect individually with each of the inflatable compartments around the face-contacting contour of the mask; central connector 105 that connects the main body of the mask with the breathable gas tube; and an outer ring 205 around the central connector that contains the small tubes in a configuration that is parallel to, and evenly-distributed around the circumference of, the circular wall of the breathable gas tube. The small tubes turn outwards toward the viewer within outer ring 205 and thus appear in cross-sectional form in this part of FIG. 2. The inflatable compartments around the face-contacting contour (perimeter) of the mask, including 201 and 203, may be made from material selected from the group consisting of: latex, nylon, polyethylene terephthalate, and polyvinyl chloride.

In this example, the inflatable compartments around the face-contacting contour (perimeter) of the mask, such as compartments 201 and 203, are contiguous but separate. In this example, each of these inflatable compartments, such as 201 or 203, is individually expandable by filling it with a pressurized gas conducted to the compartment by one of the small tubes, such as small tube 202 or 204. In another example, the compartments may be expanded by filling with a flowable liquid or gel. The ability to differentially and selectively adjust the size and/or shape of each of these inflatable compartments by individually adjusting the pressure within each compartment allows customization of the shape of the perimeter of the mask to better fit the contours of an individual's face while the mask is being worn. This helps to avoid areas of excess pressure (that can cause skin irritation and pain) and to avoid areas of inadequate pressure (that can cause air leaks). This can improve the comfort of the mask, increase patient compliance with tolerating wearing a mask, and improve the therapeutic efficacy of wearing a mask.

In this example, pressurized air flows to inflate compartments, such as 201 or 203, travel toward the main body of the mask through small tubes, including small tubes 202 and 204, that travel in parallel to central gas tube 106. In some respects this configuration is analogous to the way in which nutrients flow through tubes in a ring of bark around a tree trunk. This configuration appears in the cross-sectional display within outer ring 205 in FIG. 2. In some respects, this cross-section is similar to what one sees when one cuts a cross-section of a tree trunk, with the inner gas tube being analogous to the inner trunk core and the outer small tubes being analogous to nutrient conduits in the ring of bark around the trunk. When these small tubes reach the main body of the mask, they bend outwardly in radial spokes to connect with the inflatable compartments around the perimeter of the mask, including 201 and 203. There is one small tube per inflatable compartment. In another example, the smaller tubes could reach the main body of the mask in a bundle that is separate from central tube 106. There are different types of pumps and other means for creating different pressure levels in the small tubes and the precise means of creating different pressure levels is not central to this invention, so this description does not specify the particular component at the end of the small tubes that is distant from the mask.

In this example, the face-contacting contour (perimeter) of the mask is comprised of a series of contiguous, but segmented, inflatable compartments that can be differentially and selectively inflated. In another example, the face-contracting contour (perimeter) of the mask may be comprised of segments that are moved by filling with fluid or other hydraulic means, by magnetic force, or by the operation of small electromechanical motors such as Micro Electrical Mechanical Systems (MEMS). In an example using MEMS, the inflatable compartments 201 and 203 could be replaced by compartments that are expanded by microscale electromechanical pistons and the small tubes 202 and 204 could be replaced by wires that conduct electricity to these pistons.

In this example, the face-contacting contour of the mask is customized to better fit the person's face by differentially and selectively moving members that are located around the perimeter of the face-contacting contour of the mask. In another example, a mask may be customized to better fit a person's face by differentially and selectively moving members that are not directly on the perimeter of the face-contacting contour of the mask, but whose differential and selective movement nonetheless changes the perimeter of the face-contacting contour of the mask. In this example, the differentially and selectively movable members, including 201 and 203 are in direct contact with the person's face. In another example, there may be a flexible layer between these members and the person's face. In this example, the movable members are contiguous. In another example, these members may be separated by a non-adjustable segment or membrane.

In this example, inflation of a inflatable compartment increases both the pressure on the person's face in the location of that compartment and also increases the width of the mask perimeter in that location. In other examples, differential and selective movement of members around the face-contacting (perimeter) of the mask may change the contour of the mask in other ways. These other ways to change the contour of the mask may be selected from group consisting of different levels of pressure between the mask and the person's face at different locations around the face-contacting contour of the mask; different segment curvatures at different locations around the face-contacting contour of the mask; different radial distances from the center of the mask to the perimeter of the mask at different locations around the face-contacting contour of the mask; and different widths of contact between the mask and the person's face at different locations around the face-contacting contour of the mask.

In this example, each of the movable members is individually adjustable. In another example, some of the members may be adjusted in groups as long as there are at least two groups that are differentially and selectively movable. In another example, one may add pressure sensors to measure the pressure within each of these inflatable members in order to better control pressure differentials among the members. In another example, one may attach flow sensors to each movable member in order to detect air flow between the surface of that member and the person's face in order to automatically detect leaks.

Having differentially and selectively movable members around the face-contacting contour (perimeter) of the mask allows a better and more comfortable seal than is possible with methods that rely on straps to hold the mask against one's face. One can adjust the overall position and pressure of a standard respiratory mask by adjusting straps, but there are limits to how accurately the straps can change the face-contacting contour of a standard mask. If one can only adjust the overall position and pressure of the mask, then one may not be able to correct various spots around the mask perimeter with too little pressure (causing leaks) or too much pressure (causing pain and skin irritation) based on the unique contours of one's face.

Having differentially and selectively adjustable members around the perimeter of the mask also allows a better seal than is possible with a single inflatable ring or a single compressible gel ring. With a single inflatable ring, it can be difficult or impossible to find a single inflation pressure that stops leaks at spots where there is a gap between the mask surface and face without pinching or overly compressing the skin at other spots. Different people have differently-shaped faces with different contours, creases, and protrusions. These variations can change over time with changes in weight. They can even change during the night as a person changes their sleeping position with their head against a pillow at different angles.

Having differentially and selectively adjustable members around the perimeter of the mask also is also superior to methods using a one-time face-molding process to create a custom-fitted mask. One-time molding processes use moldable materials that change from a relatively soft and moldable state to a relative hard and fixed state. These materials are generally pressed against a person's face when the materials are in the relatively-soft state so that the materials conform to the contours of that person's face. The materials are then removed from the person's face and harden into a relatively-hard state, keeping a molded contour of that person's face. These materials in their hardened state are then used to create a customized mask directly, by incorporation into a mask, or indirectly, by a second-stage molding process to create materials that are then incorporated into a mask. There are three reasons why this present invention has several advantages over the use of moldable materials to make customized masks in the prior art:

First, this present invention allows real-time adjustment of the contours of the mask while it is being worn. A mask formed from a one-time molding process does not allow real-time adjustments. Such real-time adjustments are especially important when: the pressure of the mask on the face when used regularly changes from the pressure applied in the one-time molding process; and the contours of the person's face change from its contours during the one-time molding process, such as when a person sleeps on their side with their face on a pillow or when their weight varies. Further, with this invention, a device could be connected to the mask to monitor the pressure levels of the individual members, to detect gas leakage, and to automatically adjust those individual pressure levels to stop leaks while a person sleeps. This is not possible with a one-time molding process.

Second, this present invention avoids the time and expense of moldable material preparation, pressing, and mask formation in the custom molding process. For example, a person is much more likely to be able to self-adjust the present invention while wearing the mask than to self-apply and remove a moldable mask from their own face. The custom molding process is likely to involve the time and expense of professional assistance in a health care setting, but the present invention can be customized in the person's own home.

Thirdly, this present invention avoids: placement of potentially sticky or irritating chemicals in contact with the person's skin; the delay of waiting for the moldable substance to harden; and undesirable changes in the shape of the mask between the time it is pressed against the person's face and when it hardens. Undesirable changes in the shape of the mask can occur due to contact of the mask with a support surface if the mask is placed on a support surface or the force of gravity acting on soft material even if the mask is suspended while hardening.

Figure 3:
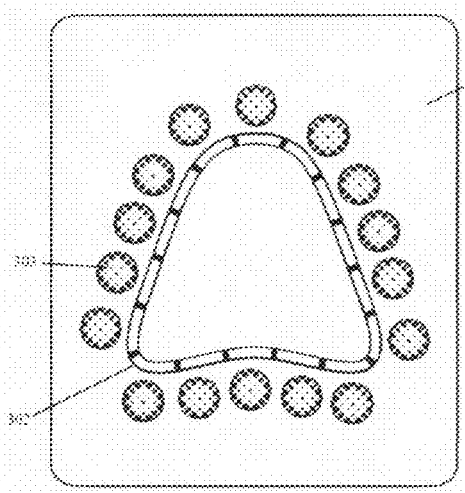
FIGS. 3 and 4 show one example of a user interface for the mask and how it may be used to custom fit the mask.
Figure 3:
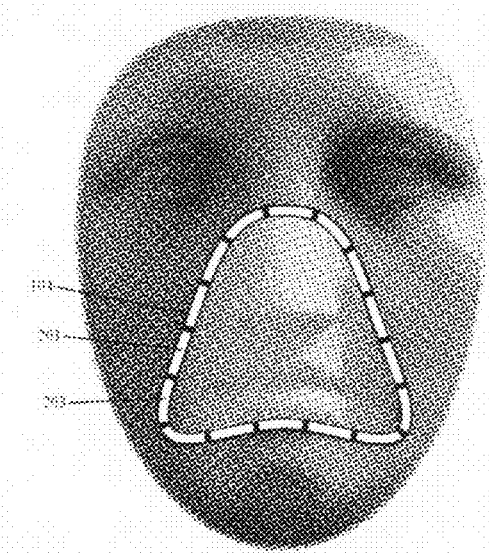
Figure 4:
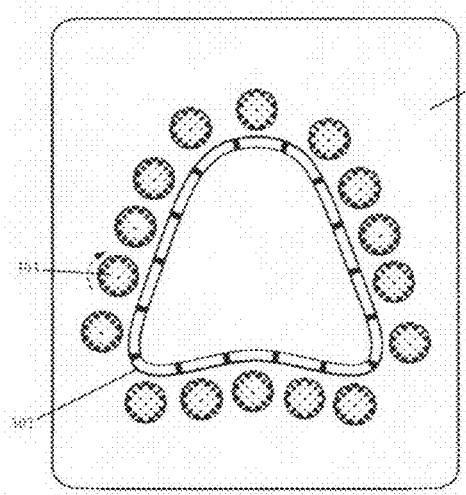
Figure 4:
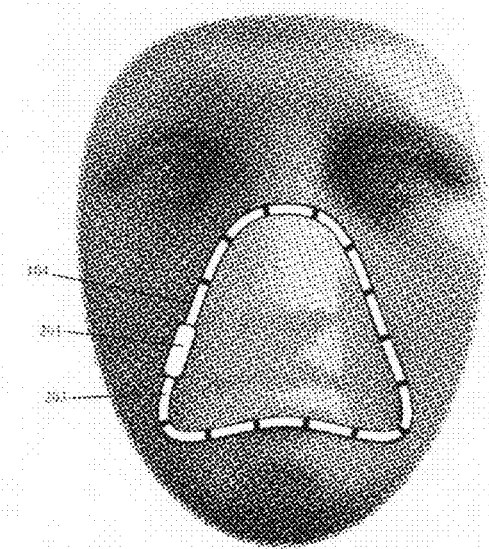

FIGS. 3 and 4 show one embodiment of the user interface claimed in this invention and how it may be used to customize the fit of the mask by differentially and selectively adjusting movable members around the face-contacting contour (perimeter) of the mask. The left sides of FIGS. 3 and 4 show a user interface on a remote control unit and the right sides of FIGS. 3 and 4 show the effects of manipulating the user interface on the face-contacting contour (perimeter) of the mask. In FIGS. 3 and 4, in order to focus on the relationship between the user interface on the remote control unit and the corresponding changes in the face-contacting contour (perimeter) of the mask, the mask and gas flow tube are shown as being transparent except for the series of inflatable compartments around the face-contacting contour (perimeter) of the mask.

FIG. 3 shows control unit 301 with a user interface that includes: image 302 of the compartments around the face-contacting contour (perimeter) of the mask; and a series of control knobs associated with the image, including knob 303, wherein each knob controls the inflation of one compartment. In this example, turning a knob on the control unit clockwise inflates the corresponding compartment on the contour (perimeter) of the mask and turning that knob counter-clockwise deflates that corresponding compartment. For example, as shown in FIG. 4, turning knob 303 clockwise increases the inflation of compartment 201. By differentially and selectively adjusting the different knobs on the control unit one can differentially and selectively inflate or deflate the different compartments around the face-contacting contour (perimeter) of the mask. This allows one to customize the contour of the mask to the contour of the face, in real time, in order to reduce leaks from spots with too little pressure on the skin and to reduce skin irritation from spots with too much pressure on the skin.

There are many methods in the prior art, including controllable air pumps, by which inflation of a compartment can be changed by manipulation of a knob, switch, or other user interface and the exact means by which manipulation of the user interface results in changes in the movable member around the face-contacting contour (perimeter) of the mask is not central to this invention. Accordingly, this means is not specified in this description. The novel features of this invention involve the interaction between manipulation of the user interface and the resulting changes in the contour (perimeter) of the mask, which are shown in FIGS. 3 and 4.

Figure 5:
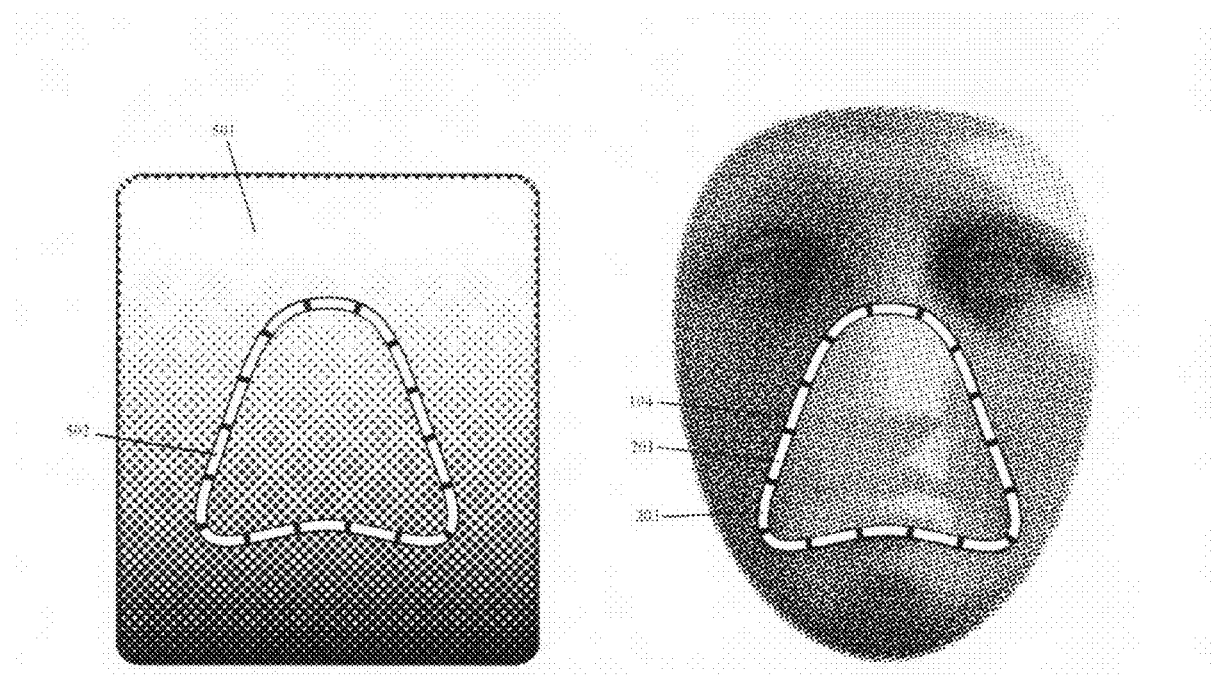
FIGS. 5 and 6 show another example of a user interface for the mask and how it may be used to custom fit the mask.
Figure 6:
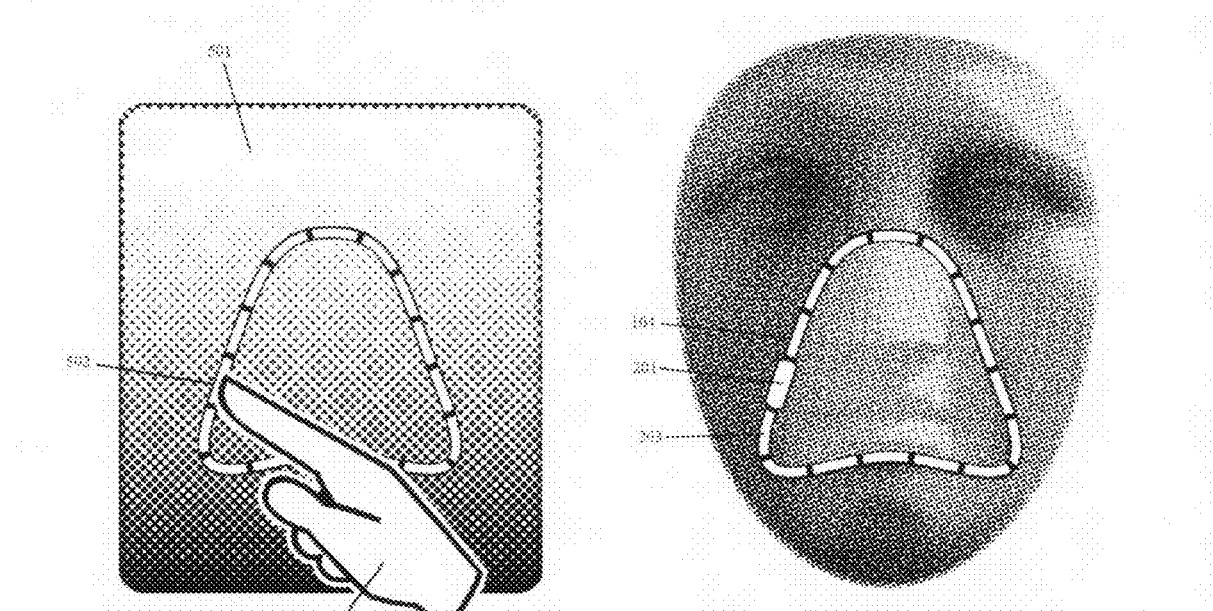

FIGS. 5 and 6 show another example of how the user interface claimed in this invention may be embodied. In FIGS. 5 and 6, the control unit 501 has a touch-screen user interface that displays an image 502 of the face-contacting contour (perimeter) of the mask. In this example, as shown in FIG. 6, touching one of the compartments on the image on the screen, such as compartment 502, triggers inflation of the corresponding compartment, 201, on the actual face-contacting contour (perimeter) of the mask. In an example, the control unit may have a toggle switch to switch from touch causing inflation to touch causing deflation. In another example, there may be inflation and deflation touch buttons for each compartment shown on the touch screen. In another example, inflation or deflation of a compartment may be controlled by moving a cursor on a non-touch-sensitive screen and double-clicking, using a device such as a computer mouse. In other examples, the control unit and user interface may use other interface methods such as buttons, switches, sliding controls, touch pads, keypads, keyboards, joysticks, track balls, motion capture cameras, gesture recognition, motion recognition gloves, motion recognition clothing, and accelerometer-based devices.

I claim:

1. A respiration-related mask that can be custom fitted to a person's face to reduce leaks and skin irritation comprising:
    two or more differentially and selectively movable members that are part of a respiration-related mask, wherein differential and selective movement of these members changes the face-contacting contour of the mask; and
    a user interface that allows the person to differentially and selectively adjust the movable members so as to better fit the face-contacting contour of the mask to the person's face while the person is wearing the mask.

2. The respiration-related mask with a user interface in claim 1 wherein the differentially and selectively movable members are located along the face-contacting contour of the mask that defines a space that channels the breathable gas into the person's nose, mouth, or both.

3. The respiration-related mask with a user interface in claim 1 wherein the differentially and selectively movable members can be differentially and selectively moved by one or more means selected from the group consisting of: inflation by a gas, or other pneumatic means; expansion by a liquid or gel, or other hydraulic means; movement by magnetic force; and the operation of Micro Electrical Mechanical Systems (MEMS).

4. The respiration-related mask with a user interface in claim 1 wherein adjustment of the differentially and selectively movable members is selected from the group consisting of: different levels of pressure between the mask and the person's face at different locations around the face-contacting contour of the mask; different segment curvatures at different locations around the face-contacting contour of the mask; different radial distances from the center of the mask to the perimeter of the mask at different locations around the face-contacting contour of the mask; and different widths of contact between the mask and the person's face at different locations around the face-contacting contour of the mask.

5. The respiration-related mask with a user interface in claim 1 wherein movement of the differentially and selectively movable members is controlled by a remote control unit, at least ten inches away from the main body of the mask, that transmits control signals through wires, wireless transmission, or fiber optics.

6. The respiration-related mask with a user interface in claim 1 wherein movement of the differentially and selectively movable members is controlled by one or more interface features selected from the group consisting of: knob; button; switch; sliding control; display screen; touch screen; computer mouse; touch pad; keypad; keyboard; joystick; track ball; motion capture; gesture recognition; motion recognition glove; motion recognition clothing; and accelerometer.

7. The respiration-related mask with a user interface in claim 1 wherein movement of the differentially and selectively movable members occurs in real time.

8. The respiration-related mask with a user interface in claim 1 wherein, in addition to manual adjustment of the differentially and selectively movable members, adjustment of the differentially and selectively movable members can also be set to occur automatically in real time to eliminate leaks that are automatically detected or to automatically alleviate places where tissue is too compressed, by automatically adjusting the differentially and selectively moveable members on the face-contacting contour of the mask.

9. A respiration-related mask that can be custom fitted to a person's face to reduce leaks and skin irritation comprising:
two or more differentially and selectively movable members that are part of a respiration-related mask,
wherein differential and selective movement of these members changes the face-contacting contour of the mask;
wherein these members are located along the face-contacting contour of the mask that defines a space that channels the breathable gas into the person's nose, mouth, or both; and
wherein these members can be differentially and selectively moved by one or more means selected from the group consisting of: inflation by a gas, or other pneumatic means; expansion by a liquid or gel, or other hydraulic means; movement by magnetic force; and the operation of Micro Electrical Mechanical Systems (MEMS);
and a user interface that allows the person to differentially and selectively adjust the movable members so as to better fit the face-contacting contour of the mask to the person's face while the person is wearing the mask.

10. The respiration-related mask with a user interface in claim 9 wherein adjustment of the differentially and selectively movable members is selected from the group consisting of: different levels of pressure between the mask and the person's face at different locations around the face-contacting contour of the mask; different segment curvatures at different locations around the face-contacting contour of the mask; different radial distances from the center of the mask to the perimeter of the mask at different locations around the face-contacting contour of the mask; and different widths of contact between the mask and the person's face at different locations around the face-contacting contour of the mask.

11. The respiration-related mask with a user interface in claim 9 wherein movement of the differentially and selectively movable members is controlled by a remote control unit, at least ten inches away from the main body of the mask, that transmits control signals through wires, wireless transmission, or fiber optics.

12. The respiration-related mask with a user interface in claim 9 wherein movement of the differentially and selectively movable members is controlled by one or more interface features selected from the group consisting of: knob; button; switch; sliding control; display screen; touch screen; computer mouse; touch pad; keypad; keyboard; joystick; track ball; motion capture; gesture recognition; motion recognition glove; motion recognition clothing; and accelerometer.

13. respiration-related mask with a user interface in claim 9 wherein movement of the differentially and selectively movable members occurs in real time.

14. The respiration-related mask with a user interface in claim 9 wherein, in addition to manual adjustment of the differentially and selectively movable members, adjustment of the differentially and selectively movable members can also be set to occur automatically in real time to eliminate leaks that are automatically detected or to automatically alleviate places where tissue is too compressed, by automatically adjusting the differentially and selectively moveable members on the face-contacting contour of the mask.

15. A respiration-related mask that can be custom fitted to a person's face to reduce leaks and skin irritation comprising:
two or more differentially and selectively movable members that are part of a respiration-related mask,
wherein differential and selective movement of these members changes the face-contacting contour of the mask;
wherein these members are located along the face-contacting contour of the mask that defines a space that channels the breathable gas into the person's nose, mouth, or both; and
wherein these members can be differentially and selectively moved by one or more means selected from the group consisting of: inflation by a gas, or other pneumatic means; expansion by a liquid or gel, or other hydraulic means; movement by magnetic force; and the operation of Micro Electrical Mechanical Systems (MEMS);
and a user interface that allows the person to differentially and selectively adjust the movable members so as to better fit the face-contacting contour of the mask to the person's face while the person is wearing the mask,
wherein movement of the differentially and selectively movable members is controlled by a remote control unit, at least ten inches away from the main body of the mask, that transmits control signals through wires, wireless transmission, or fiber optics.

16. The respiration-related mask with a user interface in claim 15 wherein adjustment of the differentially and selectively movable members is selected from the group consisting of: different levels of pressure between the mask and the person's face at different locations around the face-contacting contour of the mask; different segment curvatures at different locations around the face-contacting contour of the mask; different radial distances from the center of the mask to the perimeter of the mask at different locations around the face-contacting contour of the mask; and different widths of contact between the mask and the person's face at different locations around the face-contacting contour of the mask.

17. The respiration-related mask with a user interface in claim 15 wherein movement of the differentially and selectively movable members is controlled by one or more interface features selected from the group consisting of: knob; button; switch; sliding control; display screen; touch screen; computer mouse; touch pad; keypad; keyboard; joystick; track ball; motion capture; gesture recognition; motion recognition glove or clothing; and accelerometer.

18. The respiration-related mask with a user interface in claim 15 wherein movement of the differentially and selectively movable members occurs in real time.

19. The respiration-related mask with a user interface in claim 15 wherein, in addition to manual adjustment of the differentially and selectively movable members, adjustment of the differentially and selectively movable members can also be set to occur automatically in real time to eliminate leaks that are automatically detected or to automatically alleviate places where tissue is too compressed, by automatically adjusting the differentially and selectively moveable members on the face-contacting contour of the mask.

* * * * *